United States Patent
Kjell et al.

(10) Patent No.: US 6,541,668 B1
(45) Date of Patent: Apr. 1, 2003

(54) METHODS FOR PREPARING 3-ARLOXY-3-ARYLPROPYLAMINES AND INTERMEDIATES THEREOF

(75) Inventors: Douglas Patton Kjell, West Lafayette, IN (US); Kurt Thomas Lorenz, Lafayette, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/936,468

(22) PCT Filed: Mar. 22, 2000

(86) PCT No.: PCT/US00/06423

§ 371 (c)(1),
(2), (4) Date: Sep. 12, 2001

(87) PCT Pub. No.: WO00/61540

PCT Pub. Date: Oct. 19, 2000

Related U.S. Application Data

(60) Provisional application No. 60/128,480, filed on Apr. 9, 1999.

(51) Int. Cl.[7] .................... C07C 213/06; C07C 217/62; C07D 333/16; C07D 333/20; C07D 333/22
(52) U.S. Cl. .................... 564/347; 564/413; 549/75
(58) Field of Search ..................... 549/75; 564/347, 564/413

(56) References Cited

U.S. PATENT DOCUMENTS

| | | | |
|---|---|---|---|
| 4,868,344 A | 9/1989 | Brown | |
| 5,104,899 A | 4/1992 | Young et al. | |
| 5,166,437 A | 11/1992 | Kairisalo et al. | |
| 5,362,886 A | 11/1994 | Berglund | |
| 5,847,214 A | * 12/1998 | Arosio et al. ............... | 564/347 |

FOREIGN PATENT DOCUMENTS

| | | | | |
|---|---|---|---|---|
| EP | 0 052 492 B1 | 2/1984 | ........... | C07C/93/06 |
| ES | 2 120 368 | 10/1998 | ......... | C07C/217/48 |
| JP | 60-23656 | 6/1985 | ........... | C07C/43/20 |
| WO | 99/18947 | 4/1999 | ......... | A61K/31/135 |

OTHER PUBLICATIONS

Chumpradit, S. et al., *Iodinated Tomoxetine Derivatives as Selective Ligands for Serotonin and Norepinephrine Uptake Sites*, J. Med. Chem.(1992), 35, 4492–4497.

Corey, E. et al., *Enantioselective and Practical Syntheses of R–and S–Fluoxetines*, Tetrahedron Letters (1989), 30:39 5207–5210.

Deeter, J. et al., *Asymmetric Synthesis and Absolute Stereochemistry of LY24868*, Tetrahedron Letters (1990), 31:49, 7101–7104.

Devine, P. et al., *Stereoselective Synthesis of 2–Aryloxy Esters: An Asymmetric Approach to Fluoxetine, Tomoxetine and Nisoxetine*, Tetrahedron (1997), 53:20, 6739–6746.

Gao, Y. et al., *Asymmetric Synthesis of Both Enantiomers of Tomoxetine and Fluoxetine. Selective Reduction of 2,3–Epoxycinnamyl Alcohol with Red–A1*, J. Org. Chem. (1988) 53, 4081–4084.

Idoux, J. et al., *Aromatic Fluoroalkoxylation via Direct Aromatic Nucleophilic Substitution*, J. Org. Chem, (1983) 48, 3771–3773.

Koenig, T. et al., *A Convenient Method for Preparing Enantiomerically Pure Norfluoxetine, Fluoxetine and Tomoxetine*, Tetrahedron Letters, (1994) 35:9, 1339–1342.

Kumar, A. et al., *A New Chemoenzymatic Enantioselective Synthesis of R–(–)–Tomoxetine, (R) –and (S) –Fluoxetine*, Tetrahedron Letters, (1991) 32:16, 1901–1904.

Kumar, A. et al., *A Novel Chemoenzymatic Enantioselective Synthesis of Some Clinically Effective CNS Drugs and Related Compounds*, Indian J. Chem. (1992) 31B, 803–809.

Schneider, M. et al. *An Efficient Route to Enantiomerically Pure Antidepressants: Tomoxetine, Nisoxetine and Fluoxetine*, Tetrahedron: Assymmetry (1992) 3:4, 525–528.

Srebnik, M. et al., *Chiral Synthesis via Organoboranes*, J. Org. Chem. (1988) 53, 2916–2920.

* cited by examiner

*Primary Examiner*—Brian J. Davis
(74) *Attorney, Agent, or Firm*—Robert D. Titus; David M. Stemerick

(57) ABSTRACT

The present invention provides processes for the preparation of 3-aryloxy-3-arylpropylamines and intermediates thereof using an nucleophilic aromatic displacement in 1,3-dimethyl-2-imidazolidinone or N-methylpyrrolidinone.

9 Claims, No Drawings

METHODS FOR PREPARING 3-ARLOXY-3-ARYLPROPYLAMINES AND INTERMEDIATES THEREOF

This application claims the benefit of U.S. Ser. No. 60/128,480, filed Apr. 9, 1999.

Certain 3-aryloxy-3-arylpropylamines are known to possess central nervous system activity. See U.S. Pat. Nos. 5,744,474; 5,023,269; 4,956,388; 4,194,009; 4,314,081 and 5,658,590. The present application relates to processes for preparing 3-aryloxy-3-arylpropylamines, including duloxetine and tomoxetine.

Syntheses of 3-aryloxy-3-arylpropylamines utilizing nucleophilic aromatic displacement are known in the art. For example U.S. Pat. Nos. 5,225,585; 5,166,437; 5,023,269; 4,956,388; 5,362,886; and 5,023,269; *Tetrahedron Letters*, 31(49), 7101–7104 (1990); and PCT Publication No. WO 94/00416.

The nucleophilic aromatic displacement reaction with 3-hydroxy-3-arylpropylamines is facile for activated aryl halides. A variety of dipolar solvents, for example, dimethylsulfoxide (WO 94/00416) and 1,3-dimethyl-2-imidazolidinone and N-methylpyrrolodinone (U.S. Pat. No. 5,847,214) have been reported for the reaction of N-methyl-3-phenyl-3-hydroxypropylamine with 4-trifluoromethyl-1-chlorobenzene to give N-methyl-(4-trifluoromethylphenoxy)-3-phenylpropylamine (fluoxetine).

Nucleophilic aromatic displacement of alkoxides in 1,3-dimethyl-2-imidazolidinone are described in Japanese Kokoku Patent Publication Sho 60-23656, published Jun. 8, 1985. However, the description is limited to lower order alcohols and the exemplified preparations using unactivated aromatics are carried out at temperatures of from 160° to 190° C. in a pressure vessel reactor. See Japanese Kokoku Patent Publication Sho 60-23656, published Jun. 8, 1985, examples 7–9, 11, and 14. Thus, it does not appear that 1,3-dimethyl-2-imidazolidinone would a be useful solvent in a safe and convenient nucleophilic aromatic displacement with complex alcohols using unactivated aromatics. This is especially so for aromatics such as 2-fluorotoluene which has a boiling point of 113–114° C.

In addition, the reported reaction of unactivated substrate, 2-fluorotoluene, with the alkoxide of (S)-N-methyl-3-phenyl-3-hydroxypropylamine in dimethylsulfoxide gave a modest yield. *Tet. Let.*, 35, 1339–1342 (1994).

In spite of the difficulties with using unactivated aryl halides, a method for preparing 3-aryloxy-3-arylpropylamines using nucleophilic aromatic displacement is desirable. In contrast to methods utilizing other displacements, such as the Mitsunobu reaction or displacement of a halide by a phenol, the nucleophilic aromatic displacement method allows for cost efficient assembly of the required substituents directly from a 3-hydroxy-3-arylpropylamine.

Surprisingly, we have discovered that nucleophilic aromatic displacement using complex benzylic alcohols, such as N-methyl-3-phenyl-3-hydroxypropylamine and N,N-dimethyl-3-(2-thienyl)-3-hydroxypropylamine can be carried out with unactivated aromatics, such as 1-fluoronaphthylene and 2-fluorotoluene in 1,3-dimethyl-2-imidazolidinone or N-methylpyrrolidinone at temperatures of less than about 140° C.

The present processes provide safe and convenient methods for a high yield preparation of 3-aryloxy-3-arylpropylamines utilizing nucleophilic aromatic displacement on unactivated aromatics in 1,3-dimethyl-2-imidazolidinone or N-methylpyrrolidinone.

The present invention relates to a process for preparing a 3-aryloxy-3-arylpropylamine of the formula

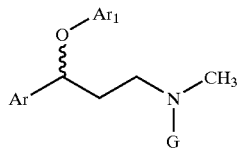

wherein

Ar is phenyl or 2-thienyl,

Ar$_1$ is 1-naphthyl, 2-methoxyphenyl, 2-thiomethoxyphenyl, or 2-methylphenyl;

G is hydrogen or methyl, and the pharmaceutically-acceptable addition salts thereof comprising the steps of:
  (a) reacting an alkoxide of a 3-hydroxy-3-arylpropylamine of the formula

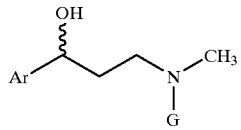

wherein
Ar and G are as defined above
with a haloaromatic of the formula

Ar$_1$—X wherein
Ar$_1$—X is 2-fluorotoluene, 2-chlorotoluene, 1-fluoronaphthalene, 1-chloronaphthalene, 2-fluoroanisole, 2-chloroanisole, 2-fluorothioanisole, or 2-chlorothioanisole, in 1,3-dimethyl-2-imidazolidinone or N-methylpyrrolidinone to give the 3-aryloxy-3-arylpropylamine;
  (b) optional N-demethylated of the 3-aryloxy-3-arylpropylamine wherein G is methyl to give the 3-aryloxy-3-arylpropylamine wherein G is hydrogen;
  (c) optional resolution of the 3-aryloxy-3-arylpropylamine to give a specific isomer of the 3-aryloxy-3-arylpropylamine; and
  (d) optional formation of an acid addition salt using a pharmaceutically-acceptable acid.

That is, the present invention provides a process for preparing a 3-aryloxy-3-arylpropylamine, as defined above and the pharmaceutically acceptable salts thereof, which comprises reacting an alkoxide of 3-hydroxy-3-arylpropylamine of the formula

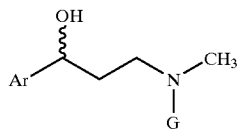

wherein

Ar and G are as defined above with a haloaromatic as defined above, characterized in that, 1,3-dimethyl-2-imidazolidinone or N-methylpyrrolidinone is used as solvent.

Particularly, the present invention relates to a process for preparing tomoxetine and the pharmaceutically-acceptable addition salts thereof comprising the steps of:

(a) reacting an alkoxide of N-methyl-3-phenyl-3-hydroxypropylamine with 2-fluorotoluene in 1,3-dimethyl-2-imidazolidinone to give N-methyl-3-(2-methylphenoxy)-3-phenylpropylamine;

(b) resolution of N-methyl-3-(2-methylphenoxy)-3-phenylpropylamine to give (R)-N-methyl-3-(2-methylphenoxy)-3-phenylpropylamine (tomoxetine); and (c) optional formation of an acid addition salt using a pharmaceutically-acceptable acid.

The present invention also relates to a particular process for preparing tomoxetine and the pharmaceutically-acceptable addition salts thereof comprising the steps of:

(a) reacting an alkoxide of N,N-dimethyl-3-phenyl-3-hydroxypropylamine) with 2-fluorotoluene in 1,3-dimethyl-2-imidazolidinone to give N,N-dimethyl-3-(2-methylphenoxy)-3-phenylpropylamine;

(b) N-demethylated N,N-dimethyl-3-(2-methylphenoxy)-3-phenylpropylamine to give N-methyl-3-(2-methylphenoxy)-3-phenylpropylamine;

(c) resolution of N-methyl-3-(2-methylphenoxy)-3-phenylpropylamine to give (R)-N-methyl-3-(2-methylphenoxy)-3-phenylpropylamine (tomoxetine); and (d) optional formation of an acid addition salt using a pharmaceutically-acceptable acid.

That is, the present invention relates to processes for preparing tomoxetine and the pharmaceutically-acceptable addition salts thereof, which comprises, reacting an alkoxide of N-methyl-3-phenyl-3-hydroxypropylamine, or an N-protected derivative thereof, with 2-fluorotoluene, characterized in that, 1,3-dimethyl-2-imidazolidinone is used as solvent.

As used herein, the following terms have the meanings indicated:

(a) the term "DMI" refers to 1,3-dimethyl-2-imidazolidinone;

(b) the term "NMP" refers to N-methylpyrrolidinone;

(c) the term "ee" or "enantomeric excess" refers to the percent by which one enantomeric, $E_1$, is in excess in a mixture of both enantiomers ($E_1+E_2$), as calculated by the equation $\{(E_1-E_2).(E_1+E_2)\}\times 100\% = ee$;

(d) the term "pharmaceutically-acceptable addition salt" refers to an acid addition salt using a pharmaceutically-acceptable acid.

The 3-aryloxy-3-arylpropylamines and the intermediates described herein form pharmaceutically acceptable acid addition salts with a wide variety of organic and inorganic acids and include the physiologically acceptable salts which are often used in pharmaceutical chemistry.

A pharmaceutically-acceptable addition salt is formed from a pharmaceutically-acceptable acid as is well known in the art. Such salts are also part of this invention. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, propiolate, propionate, phenylpropionate, salicylate, sebacate, succinate, suberate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

The present invention relates to processes for the preparation of 3-aryloxy-3-arylpropylamines. It is understood by the skilled person that these compounds exist as stereoisomers. Herein, the Cahn-Prelog-Ingold designations of (R)- and (S)- are used to refer to specific isomers where designated. Specifically, present invention relates to processes for the preparation of duloxetine, (S)-N-methyl-3-(1-naphthyloxy)-3-(2-thienyl)propylamine; and tomoxetine, (R)-N-methyl-3-(2-methylphenoxy)-3-phenylpropylamine. As will be appreciated by the skilled artisan, the present processes are not necessarily limited to the preparation of racemic mixtures or specific isomers. Rather the present processes are capable of preparing both specific enantiomers and racemic mixtures.

The specific isomers can be obtained by resolution of the product, intermediates, or in some cases the starting materials. For example, duloxetine specific isomers can be most conveniently obtained by utilizing enantomerically pure starting materials, specifically, (S)-N,N-dimethyl-3-(2-thienyl)-3-hydroxypropylamine or (R)-N-methyl-3-phenyl-3-hydroxypropylamine. As used herein the term "enantiomerically pure" refers to an enatiomeric excess which is greater than 90%, preferably greater than 93%, more preferably greater than 95%.

The present preparation of 3-aryloxy-3-arylpropylamines are carried out according to Reaction Scheme A below. In Reaction Scheme A, all substituents, unless otherwise indicated, are as previously defined. In Reaction Scheme A all reagents are well known and appreciated in the art.

Reaction Scheme A

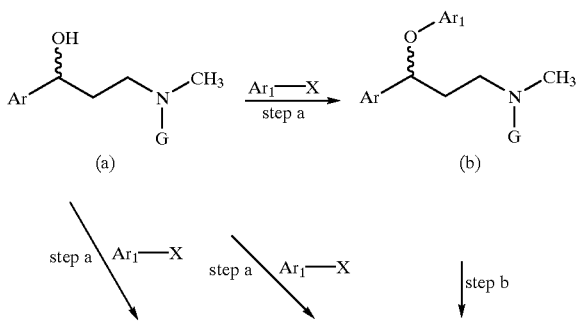

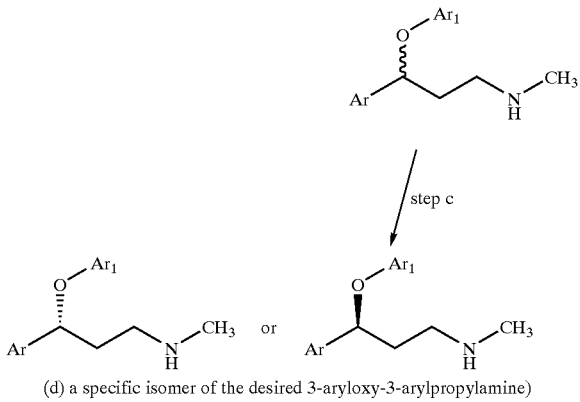

(d) a specific isomer of the desired 3-aryloxy-3-arylpropylamine)

In Reaction Scheme A, step a, a nucleophilic aromatic displacement, the alkoxide of a suitable 3-hydoxy-3-aryipropylamine of formula (a) is contacted with a suitable haloaromatic, Ar₁—X, in 1,3-dimethyl-2-imidazolidinone or N-methylpyrrolidinone to give a 3-aryloxy-3-arylpropylamine. As will be appreciated by those skilled in the art, a 3-hydoxy-3-arylpropylamine of formula (a) in which G is methyl gives a 3-aryloxy-3-arylpropylamine of formula (b); a 3-hydoxy-3-arylpropylamine of formula (a) in which G is hydrogen gives a 3-aryloxy-3-arylpropylamine of formula (c); and a specific isomer of a 3-hydoxy-3-arylpropylamine of formula (a) in which G is hydrogen gives directly a 3-aryloxy3arylpropylamine of formula (d). Also, it will be appreciated by those skilled in the art that the specific isomers of formula (d) can be obtained by demethylation of a 3-aryloxy-3-arylpropylamine of formula (b) prepared from a single isomer of a compound of formula (a) in which G is methyl.

Suitable 3-hydoxy-3-arylpropylamines of formula (a) include N,N-dimethyl-3-phenyl-3-hydroxypropylamine, N-methyl-3-phenyl-3-hydroxypropylamine, N,N-dimethyl-3-(2-thienyl)-3-hydroxypropylamine, (R)-N,N-dimethyl-3-phenyl-3-hydroxypropylamine, (R)-N-methyl-3-phenyl-3-hydroxypropylamine, (R)-N,N-dimethyl-3-(2-thienyl)-3-hydroxypropylamine, (S)-N,N-dimethyl-3-phenyl-3-hydroxypropylamine, (S)-N-methyl-3-phenyl-3-hydroxypropylamine, and (S)-N,N-dimethyl-3-(2-thienyl)-3-hydroxypropylamine. Suitable haloaromatics, include 2-fluorotoluene, 2-chlorotoluene, 1-fluoronaphthalene, 1-chloronaphthalene, 2-fluoroanisole, 2-chloroanisole, 2-fluorothioanisole, and 2-chlorothioanisole.

For example, the reaction is carried out using an alkoxide of an alcohol of formula (a). While many metals are suitable for this reaction, generally, an alkali metal alkoxide is used, with the lithium, sodium, and potassium alkoxide being preferred. Sodium and potassium alkoxide are more preferred. The alkoxide is formed by contacting of an alcohol of formula (a) with a suitable base, such as lithium hydride, lithium N,N-diisopropylamide, sodium hydride, potassium hydride, sodium hydroxide, potassium hydroxide, sodium amide, potassium amide, sodium alkoxides, such as sodium t-butoxide, sodium methoxide, sodium ethoxide, potassium alkoxides, such as potassium t-butoxide, potassium methoxide, potassium ethoxide, and the like. From 1 molar equivalent to a large molar excess of base is used. In some cases, when sodium bases are used, the addition of a catalytic amount of potassium ion can advantageously be added, for example, in the form of potassium benzoate.

The reaction is carried out in 1,3-dimethyl-2-imidazolidinone or N-methylpyrrolidinone. Neither high temperatures nor pressure vessels are required. The reaction is carried out at temperatures of from about 0° C. to about 140° C. with temperatures of from about 20° C. to about 130° C. being preferred, and temperatures of from about 80° C. to about 120° C. being more preferred. The reaction typically requires from about 1 hour to about 48 hours. The product can be isolated and purified by techniques well known in the art, such as filtration, evaporation, extraction, trituration, chromatography, and crystallization. Alternately, the compound of formula (b) can be taken directly to step c, if desired, without isolation or without purification.

In Reaction Scheme A, optional step b, the compound of the formula (b) is N-demethylated to give the compound of formula (c). As is understood from Reaction Scheme A, where a specific isomer of compound (a) is used to provide a specific isomer of compound (b) the isomer can by N-demethylated to give compound (d) directly. Such N-demethylation reactions are well known and appreciated in the art and include demethylations which proceed through a N-cyano and carbamate intermediates followed by hydrolysis. See for example, U.S. Pat. Nos. 4,956,388; 4,314,081; and 5,362,886.

For example, a compound of formula (b) is contacted with a slight molar excess of chloro formate, such as phenyl chloroformate, ethyl chloroformate, trichloroethyl chloroformate, and the like. The reaction is carried out in the presence of a suitable base, such as triethylamine, pyridine, N,N-diisopropylethylamine, and the like. The reaction is carried out in a suitable solvent, such as toluene, dichloromethane, tetrahydrofuran, and the like. Typically the reaction is carried out at temperatures of from about 0° C. to the refluxing temperature of the solvent and require about 1 hour to 48 hours. The carbamate intermediate can be isolated and purified by techniques well known in the art, such as filtration, evaporation, extraction, trituration, chromatography, and crystallization. The carbamate intermediate is then hydrolyzed to give product. For example, the carbamate intermediate is contacted with an excess of sodium hydroxide or potassium hydroxide. The reaction is carried out in a suitable solvent, such as water, dimethyl sulfoxide, ethanol, dimethyl sulfoxide/water mixtures, and the like. Typically the reaction is carried out at temperatures of from about 20° C. to about 100° C. and require about 1 hour to 48 hours. The product can be isolated and purified by techniques well known in the art, such as filtration, evaporation, extraction, trituration, chromatography, and crystallization.

In Reaction Scheme A, optional step c, a compound of formula (c) is resolved to give a 3-aryloxy-3-arylpropylamine having a specific stereochemistry. Such resolutions are well known and appreciated in the art, such as the use of mandelic acid as described in European Patent Application No. 0 052 492, published May 26, 1982, the disclosure of which is incorporated by reference. As is understood from Reaction Scheme A, a compound (b) can be resolved by the same techniques to give a specific isomer of compound (b) the isomer can by N-demethylated, if desired to give compound (d) directly.

In Reaction Scheme A, optional step d, not shown, an acid addition salt is formed using a pharmaceutically-acceptable acid. As is appreciated by the person skilled in the art, an acid addition salt can be formed for the end products of formula (b), (c), and (d). The formation of acid addition salts is well known and appreciated in the art.

In particular, the present preparations of tomoxetine are carried out according to Reaction Scheme B below. In Reaction Scheme B, all substituents, unless otherwise indicated, are as previously defined. In Reaction Scheme B all reagents are well known and appreciated in the art.

Reaction Scheme B

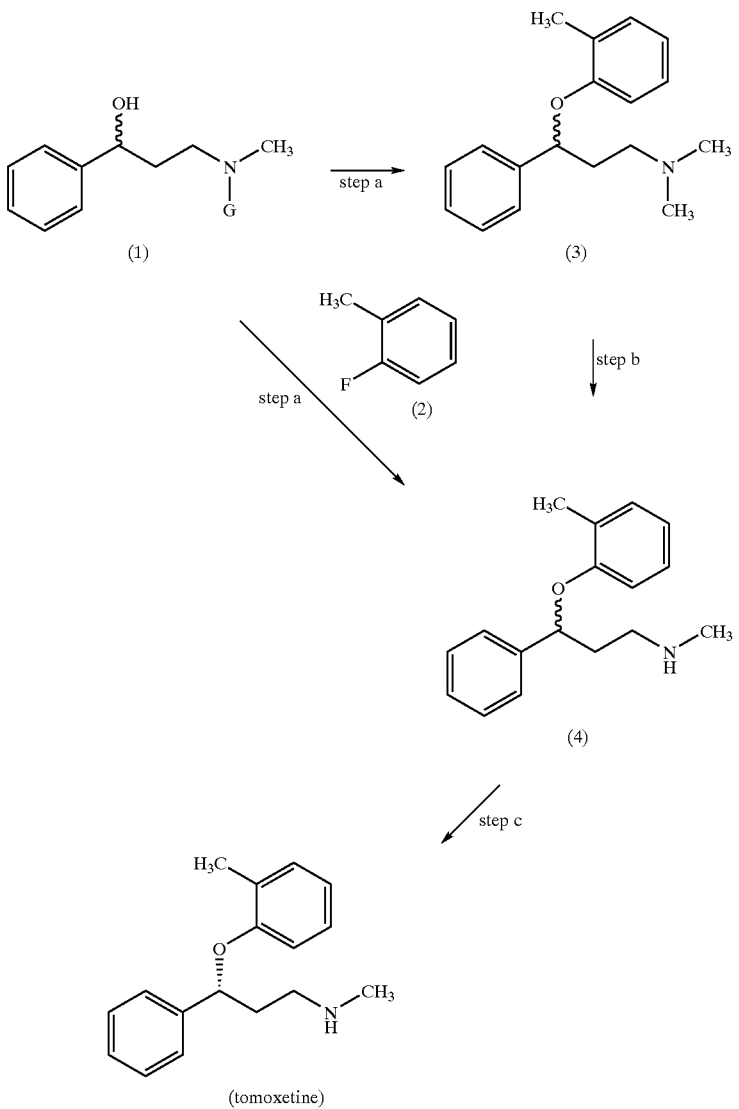

(tomoxetine)

In Reaction Scheme B, step a, a nucleophilic aromatic displacement, the alkoxide of an alcohol of formula (1) in which G is methyl or hydrogen, N,N-dimethyl-3-phenyl-3-hydroxypropylamine where G is methyl or N-methyl-3-phenyl-3-hydroxypropylamine where G is hydrogen, is contacted with a 2-fluorotoluene (the compound of formula (2)) in 1,3-dimethyl-2-imidazolidinone or N-methylpyrrolidinone to give the compound of formula (3), N,N-dimethyl-3-(2-methylphenoxy)-3-phenylpropylamine, or the compound of formula (4), N-methyl-3-(2-methylphenoxy)-3-phenylpropylamine; respectively.

For example, the reaction is carried out using an alkoxide of an alcohol of formula (1). While many metals are suitable for this reaction, generally, an alkali metal alkoxide is used, with the lithium, sodium, and potassium alkoxide being preferred. Sodium and potassium alkoxide are more preferred. The alkoxide is formed by contacting of an alcohol of formula (1) with a suitable base, such as lithium hydride, lithium N,N-diisopropylamide, sodium hydride, potassium hydride, sodium amide, potassium amide, sodium alkoxides, such as sodium t-butoxide, potassium alkoxides, such as potassium t-butoxide, and the like. From 1 molar equivalent to a large molar excess of base is used, with about 1.05 to about 1.5 molar equivalents being preferred. The reaction is carried out in 1,3-dimethyl-2-imidazolidinone or N-methylpyrrolidinone with 1,3-dimethyl-2-imidazolidinone being preferred. Neither high temperatures nor pressure apparatus are required. The reaction is carried out at temperatures of from about 75° C. to about 140° C. with temperatures of from about 90° C. to about 130° C. being preferred and about 95° C. to about 115° C. being more preferred. The reaction typically requires from about 12 hours to about 48 hours. The product can be isolated and purified by techniques well known in the art, such as filtration, evaporation, extraction, trituration, chromatography, and crystallization. Alternately, the compound of formula (4) can be taken directly to step c without isolation or without purification.

In Reaction Scheme B, step b, the compound of the formula (3), N,N-dimethyl-3-(2-methylphenoxy)-3- phenylpropylamine, is N-demethylated to give the compound of formula (4), N-methyl-3-(2-methylphenoxy)-3-phenylpropylamine. Such N-demethylation reactions are well known and appreciated in the art and include demethylations which proceed through a N-cyano and carbamate intermediates followed by hydrolysis as described above in Reaction Scheme A, step c, above.

In Reaction Scheme B, step c, N-methyl-3-(2-methylphenoxy)-3-phenylpropylamine is resolved to give (R)-N-methyl-3-(2-methylphenoxy)-3-phenylpropylamine (tomoxetine). Such resolutions are well known and appreciated in the art and is described in European Patent Application No. 0 052 492, published May 26, 1982, the disclosure of which is incorporated by reference.

In Reaction Scheme B, optional step d, not shown, an acid addition salt is formed using a pharmaceutically-acceptable acid. The formation of acid addition salts is well known and appreciated in the art.

The present invention is further illustrated by the following examples and preparations. These examples and preparations are illustrative only and are not intended to limit the invention in any way.

The terms used in the examples and preparations have their normal meanings unless otherwise designated. For example "° C." refers to degrees Celsius; "N" refers to normal or normality; "M" refers to molar or molarity; "mol" refers to mole or moles; "mmol" refers to millimole or millimoles; "kg" refers to kilogram or kilograms; "g" refers to gram or grams; "mg" refers to milligram or milligrams; "mL" refers milliliter or milliliters; "L" refers to liter or liters; "bp" refers to boiling point; "mp" refers to melting point; "brine" refers to a saturated aqueous sodium chloride solution; etc.

EXAMPLE 1

Tomoxetine, (R)-N-Methyl-3-(2-methylphenoxy)-3-phenylpropylamine Hydrochloride

Combine N-methyl-3-hydroxy-3-phenylpropylamine (10 g, 60.53 mmol) and potassium t-butoxide (7.5 g, 66.58 mmol) in 1,3-dimethyl-2-imidazolidinone (25 mL). Heat to dissolve, if necessary, before adding 2-fluorotoluene (20 mL, 181.6 mmol). Heat to about 110° C. After 20 hours, cool to ambient temperature and carefully add water and then toluene. Separate the layers and extract the organic layer with water. Evaporate by distillation to reduce the volume of the organic layer to about 10 mL, cool to about 40° to 50° C., dilute with about 4.5 volumes of ethyl acetate (about 45 mL), and add (S)-(+)-mandelic acid (5.52 g, 36.3 mmol). Hold the temperature at about 40° to 45° C. and seed with (R)-N-methyl-3-(2-methylphenoxy)-3-phenylpropylamine (S)-(+)-mandelic acid salt. After about 2 hours, cool to about 0° to 5° C. to give a solid. Collect the solid by filtration, rinse with ethyl acetate and dry in vacuo at about 80° C. Combine (R)-N-methyl-3-(2-methylphenoxy)-3-phenylpropylamine (S)-(+)-mandelic acid salt (4.36 g, 10.7 mmol), water (13.5 mL), aqueous 50% sodium hydroxide solution (0.99 g, 12.32 mmol), and methyl t-butyl ether (14 mL). Heat to about 40° to 45° C. and stir until the solids dissolve. Separate the layers and extract the organic layer with water. Dilute the organic layer with methyl t-butyl ether (about 17 mL) and dry by distillation (collecting the azeotrope). Add an additional amount of methyl t-butyl ether (about 17 mL) to bring the weight of the reaction mixture up to about 20.6 g. Add isopropanol (7.5 g) before slowly adding concentrated aqueous hydrochloric acid solution (1.11 g, 11.25 mmol) over about 3 hours. Stir the reaction mixture, cooling if necessary to give a solid. Collect the solid by filtration, rinse with methyl t-butyl ether, and dry in vacuo at about 70° to 80° C. to give the title compound.

EXAMPLE 2

Tomoxetine, (R)-N-Methyl-3-(2-methylphenoxy)-3-phenylpropylamine Hydrochloride

Combine N-methyl-3-hydroxy-3-phenylpropylamine (10 g, 60.53 mmol) and potassium t-butoxide (7.5 g, 66.58 mmol) in 1,3-dimethyl-2-imidazolidinone (25 mL). Heat to dissolve, if necessary, before adding 2-fluorotoluene (20 mL, 181.6 mmol). Heat to about 110° C. After 20 hours, cool to ambient temperature and carefully add water and then toluene. Separate the layers and extract the organic layer with water. Evaporate by distillation to reduce the volume of the organic layer until about 3 g of toluene remains. Add toluene (about 12.5 g), cool to about 40° to 50° C., dilute with ethyl acetate (about 45 g), and add (S)-(+)-mandelic acid (5.52 g, 36.3 mmol). Hold the temperature at about 40° to 45° C. and seed with (R)-N-methyl-3-(2-methylphenoxy)-3-phenylpropylamine (S)-(+)-mandelic acid salt. After about 2 hours, cool to about 0° to 5° C. to give a solid. Collect the solid by filtration, rinse with ethyl acetate and dry in vacuo at about 80° C. Combine (R)-N-methyl-3-(2-methylphenoxy)-3-phenylpropylamine (S)-(+)-mandelic acid salt (4.36 g, 10.7 mmol), water (13.5 mL), aqueous 50% sodium hydroxide solution (0.99 g, 12.32 mmol), and methyl t-butyl ether (14 mL). Heat to about 40° to 45° C. and stir until the solids dissolve. Separate the layers and extract the organic layer with water. Dilute the organic layer with methyl t-butyl ether (about 17 mL) and dry by distillation (collecting the azeotrope). Add an additional amount of methyl t-butyl ether (about 17 mL) to bring the weight of the reaction mixture up to about 20.6 g. Add isopropanol (7.5 g) before slowly adding concentrated aqueous hydrochloric acid solution (1.11 g, 11.25 mmol) over about 3 hours. Stir the reaction mixture, cooling if necessary to give a solid. Collect the solid by filtration, rinse with methyl t-butyl ether, and dry in vacuo at about 70° to 80° C. to give the title compound.

We claim:

1. A process for preparing 3-aryloxy-3-arylpropylamines of the formula

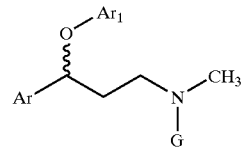

wherein
Ar is phenyl or 2-thienyl,
$Ar_1$ is 1-naphthyl, 2-methoxyphenyl, 2-thiomethoxyphenyl, or 2-methylphenyl;
G is hydrogen or methyl,
and the pharmaceutically-acceptable addition salts thereof comprising the steps of:

(a) reacting an alkoxide of a 3-hydroxy-3-arylpropylamine of the formula

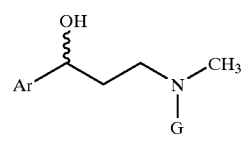

wherein
Ar and G are as defined above with a haloaromatic of the formula

Ar₁—X wherein
Arl-X is 2-fluorotoluene, 2-chlorotoluene, 1-fluoronaphthalene, 1-chloronaphthalene, 2-fluoroanisole, 2-chloroanisole, 2-fluorothioanisole, or 2-chlorothioanisole, in 1,3-dimethyl-2-imidazolidinone or N-methylpyrrolidinone at a temperature of from 0° C. to 140° C. to give the 3-aryloxy-3-arylpropylamine;

(b) N-demethylat of the 3-aryloxy-3-arylpropylamine wherein G is methyl to give the 3-aryloxy-3-arylpropylamine wherein G is hydrogen;

(c) optional resolution of the 3-aryloxy-3-arylpropylamine to give a specific isomer of the 3-aryloxy-3-arylpropylamine; and (d) optional formation of an acid addition salt using a pharmaceutically-acceptable acid.

2. A process according to claim 1 wherein 1,3-dimethyl-2-imidazolidinone is used.

3. A process according to claim 2 wherein the 3-hydroxy-3-arylpropylamine is (S)-N,N-dimethyl-3-(2-thienyl)-3-hydroxypropylamine and the haloaromatic is 1-fluoronaphtbalene.

4. A process for preparing tomoxetine and the pharmaceutically-acceptable addition salts thereof comprising the steps of:

(a) reacting an alkoxide of N-methyl-3-phenyl-3-hydroxypropylamine with 2-fluorotoluene in 1,3-dimethyl-2-imidazolidinone at a temperature of from 0° C. to 140° C. to give N-methyl-3 -(2 -methylhenoxy)-3 -phenylpropylamine;

(b) resolution of N-methyl-3-(2-methylphenoxy)-3-phenylpropylamine to give (R)-N-methyl-3-(2-methylphenoxy)-3-phenylpropylamine (tomoxetine); and (c) optional formation of an acid addition salt using a pharmaceutically-acceptable acid.

5. A process for preparing tomoxetine and the pharmaceutically-acceptable addition salts thereof comprising the steps of:

(a) reacting an alkoxide of N,N-dimethyl-3-phenyl-3-hydroxypropylaminel with 2-fluorotoluene in 1,3-dimethyl-2-imidazolidinone at a temperature of from 0° C. to 140° C. to give N,N-dimethyl-3-(?2-methylphenoxy)-3-phenylpropylaxrine;

(b) N-demethylation of N,N-dimethyl-3-(2-ntethylphenoxy)-3-phenylpropylamine to give N-methyl-3-(2-methylphenoxy)-3-phenylpropylamine;

(c) resolution of N-methyl-3-(2-methylphenoxy)-3-phenylpropylamine to give (R)-N-methyl-3-(2-methylphenoxy)-3-phenylpropylamine; and (d) optional formation of an acid addition salt using a pharmaceutically-acceptable acid.

6. A process for preparing N-methyl-3-(2-methylphenoxy)-3 phenylpropylamine coprising the steps of (a) reacting an alkoxide of N-methyl-3-phenyl-3-hydroxypropylamine at a temperature of from 0° C. to 140° C. with 2-fluorotoluene in 1,3-dimethyl-2-imidazolidinone.

7. A process for preparing N-methyl-3-42-methylphenoxy)-3-phenylpropylamine comprising the steps of:

(a) reacting an alkoxide of N,N-dimethyl-3-phenyl-3-hydroxypropylamine) with 2-fluorotoluene in 1,3-dimethyl-2-imidazolidinone at a temperature of from 0° C. to 140° C. to give N,N-dimethyl-3-(2-methylphenoxy)-3-phenylpropylamine;

(b) N-demethylation of N,N-dimethylphenoxy-3-phenylpropylamine.

8. A process for preparing 3-aryloxy-3-arylpropylazines of the formula

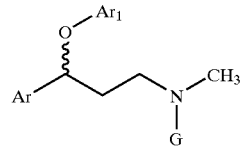

wherein
Ar is phenyl or 2-thienyl,
Ar₁ is 1-naphthyl, 2-methoxyphenyl, 2-thiomethoxyphenyl, or 2-methylphenyl;
G is hydrogen or methyl,
and the pharmaceutically acceptable salts thereof, which comprises reacting an alkoxide of N-methyl-3-hydroxy-3-arylpropylamine of the formula

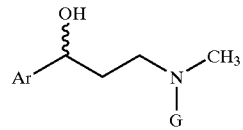

or an N-protected derivative thereof,
Ar and 0 are as defined above with an inactivated haloaromatic selected from 2-fluorotoluene, 2-chlorotoluene, 1-fluoronaphthalene, 1-chloronaphthalene, 2-fluoroanisole, 2-chloroanisole, 2-fluorothioanisole, or 2-chlorothioanisole at a temperature of from 0° C. to 140° C., characterized in that, 1,3-dimethyl-2-imidazolidinone or N-methylpyrrolidinone is used as solvent.

9. A process for preparing tomoxetine and the pharmaceutically-acceptable addition salts thereof, which comprises, reacting an alkoxide of N-methyl-3-phenyl-3-hydroxypropylamine, or an N-protected derivative thereof, with 2-fluorotoluene at a temerature of from 0° C. to 140° C., characterized in that, 1,3-dimethyl-2-imidazolidinone in used as solvent.

* * * * *